(12) United States Patent
Morales Chavarria

(10) Patent No.: US 9,339,298 B1
(45) Date of Patent: May 17, 2016

(54) DYNAMIC APPARATUS FOR DISK TRACTION

(71) Applicant: Jose Artemio Zenon Morales Chavarria, Distrito Federal (MX)

(72) Inventor: Jose Artemio Zenon Morales Chavarria, Distrito Federal (MX)

( * ) Notice: Subject to any disclaimer, the term of this patent is extended or adjusted under 35 U.S.C. 154(b) by 0 days.

(21) Appl. No.: 14/166,243

(22) Filed: Jan. 28, 2014

(51) Int. Cl.
*A61B 17/70* (2006.01)

(52) U.S. Cl.
CPC .................................. *A61B 17/7023* (2013.01)

(58) Field of Classification Search
CPC .................................................. A61B 17/7023
USPC ......................................... 606/246, 256–259
See application file for complete search history.

(56) References Cited

U.S. PATENT DOCUMENTS

| 5,810,815 A * | 9/1998 | Morales ........................ 606/250 |
| 2007/0118122 A1 * | 5/2007 | Butler et al. .................... 606/61 |

* cited by examiner

*Primary Examiner* — Pedro Philogene
*Assistant Examiner* — David C Comstock
(74) *Attorney, Agent, or Firm* — Jesus Sanchelima; Christian Sanchelima

(57) ABSTRACT

An apparatus for treating spinal vertebrae of patients that require therapeutic mechanical effects. Two interconnected articulated U-shape frame assemblies 20; 70 provide the necessary supporting at adjustable relative angular disposition with respect to each other to conform with the characteristics of the spinal segment being treated. Upper frame assembly 20 is mounted at a predetermined location of a patient's spine. Connector assemblies 40; 40' are mounted to upper assembly 20 and to telescopic tubular assembly 50 extension. Pivoting connectors 60; 60' are connected to a tubular assembly 50 and provide pivoting movement in two ortographic planes for tubular assembly 50 and lower frame assembly 70.

2 Claims, 7 Drawing Sheets

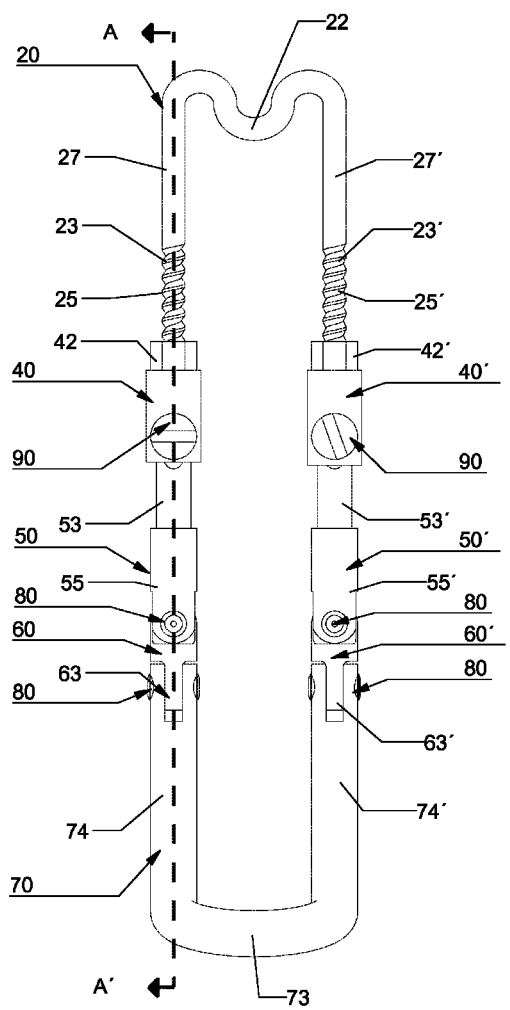
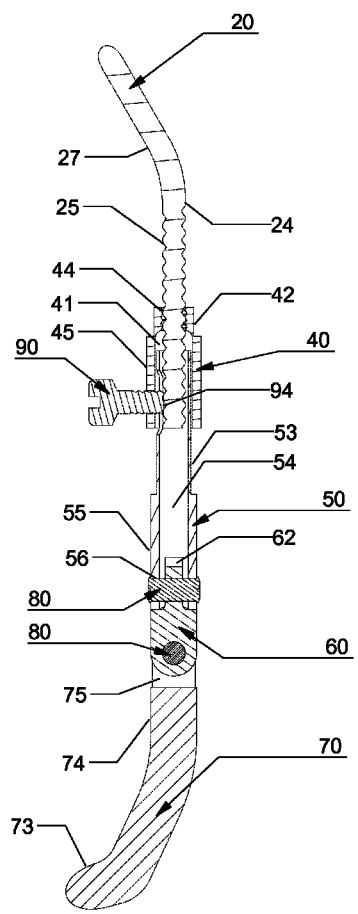

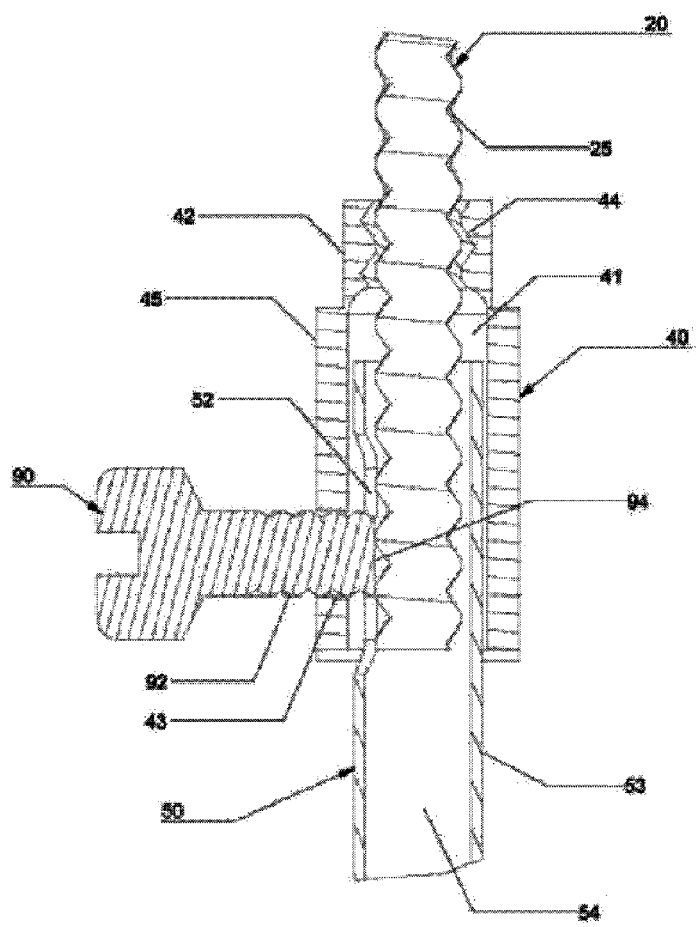

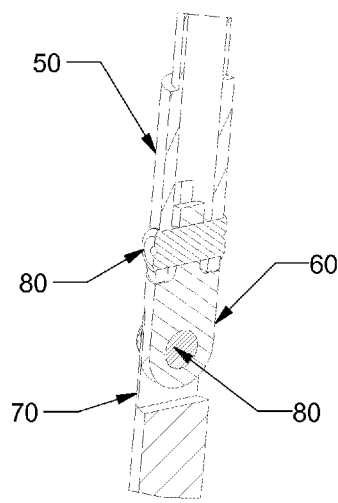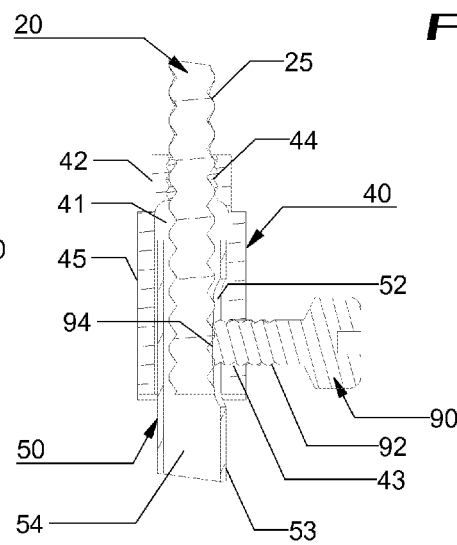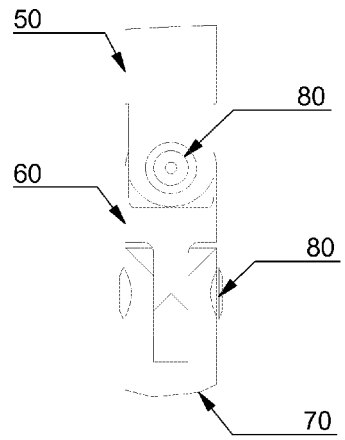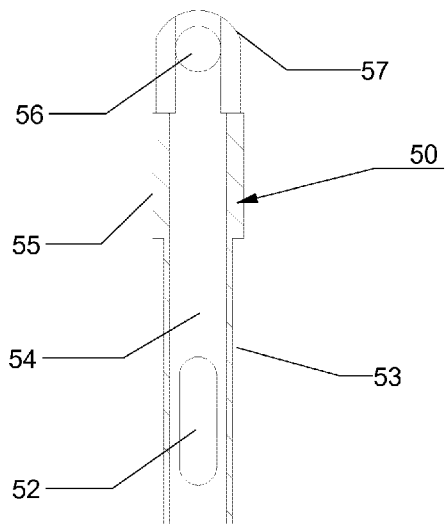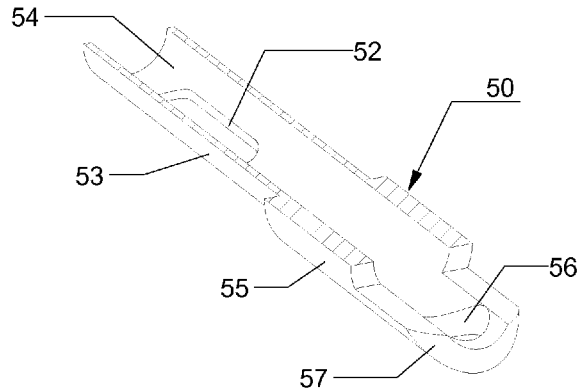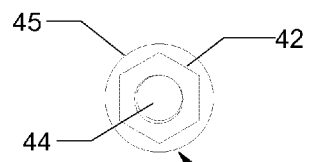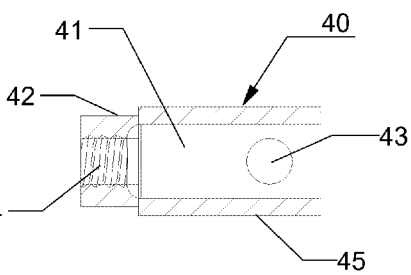

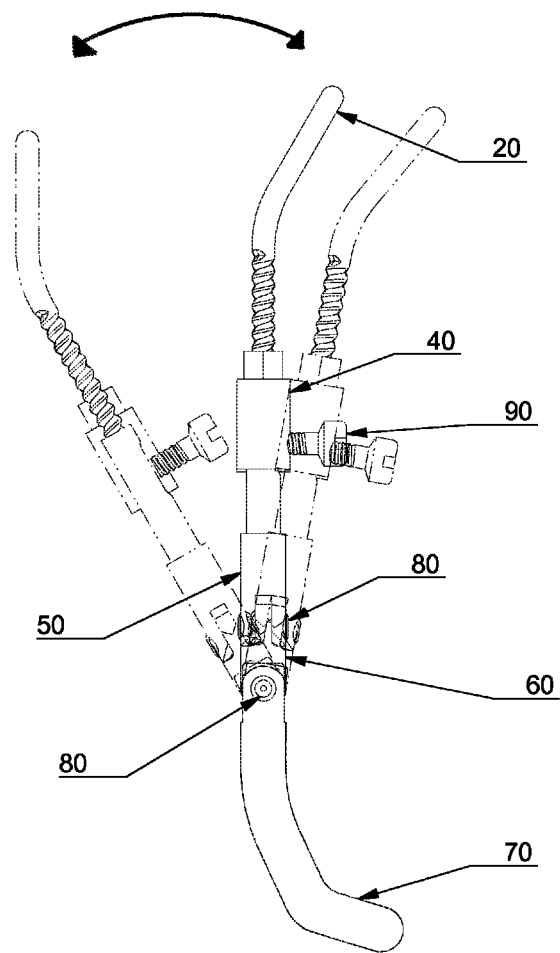

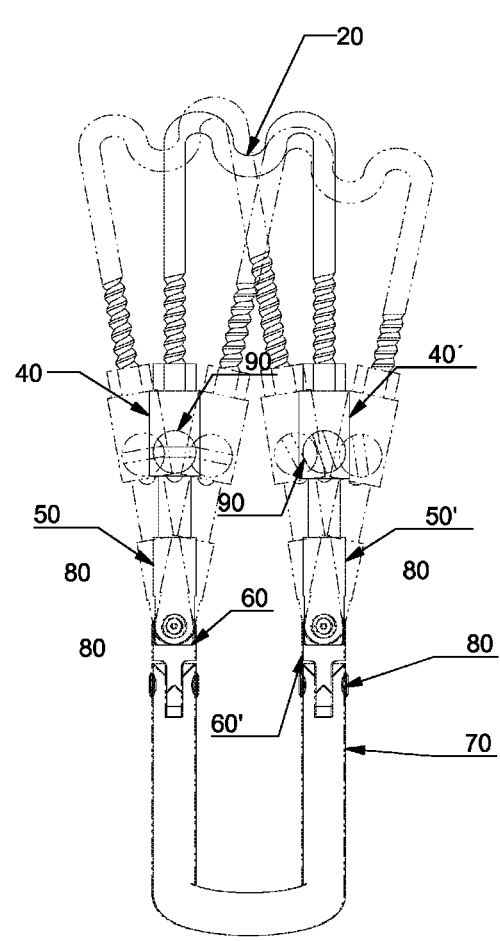

US 9,339,298 B1

DYNAMIC APPARATUS FOR DISK TRACTION

BACKGROUND OF THE INVENTION

1. Field of the Invention

The present invention relates to an orthopedic surgical apparatus for treating spinal deformities and, more particularly, to a articulated apparatus for disk traction.

2. Description of the Related Art

Several apparatuses for treating deformities have been designed in the past. None of them, however, include the articulation characteristics of the present invention providing ergonometric movements that track those naturally found in spinal segments of a patient.

Applicant believes that the closest reference corresponds to U.S. Pat. No. 5,810,815 issued to Applicant in 1998. However, it differs from the present invention because Applicant's patented surgical apparatus is not capable of dynamically follow the natural movements of a user's spine. The rigidity of the patented apparatus limits the movements allowed. These limitations are overcome with Applicant's new articulated frame apparatus for disk traction.

Other documents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide an orthopedic surgical apparatus that is used for segmental fixation of vertebrae in the spinal column.

It is another object of this invention to provide such an ergonomical apparatus that can be readily adapted to the characteristics of a user's spine providing the necessary rigidity while allowing predetermined movement tracking the spine's natural positions.

It is still another object of the present invention to provide an orthopedic surgical apparatus that can be readily mounted to a patient's body.

It is yet another object of this invention to provide such an apparatus that is inexpensive to manufacture and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 2 shows an elevational front view of the embodiment represented in the previous figure.

FIG. 2A illustrates an elevational cross-sectional view taken along line A-A' in FIG. 2.

FIG. 2B is an enlarged cross-sectional view of a connector assembly 40 mounted to threaded end 25 and tubular portion 53 partially shown.

FIG. 3A is an enlarged isometric sectional representation of portions of tubular assembly 50 and lower assembly 70, both pivotally mounted to pivoting connector assembly 60.

FIG. 3B is a longitudinal cross-sectional isometric representation of a portion of tubular assembly 50 slidably mounted threaded rod portion 25 and cylindrical portion 45.

FIG. 3C is an enlarged cross representation of pivoting connector assembly 60 with riveted pins 80.

FIG. 3D is a longitudinal cross-sectional isometric representation of tubular assembly 50.

FIG. 3E is a longitudinal cross-sectional isometric representation of assembly 50.

FIG. 3F is an end view of connector assembly 40.

FIG. 3G is a longitudinal cross-sectional isometric representation of assembly 40.

FIG. 4 shows a side elevational view of the embodiment of the apparatus represented in the previous figures in three different positions (one with solid lines and the other one two broken lines) illustrating its dynamic orthopedic capabilities.

FIG. 5 shows an elevational front view of the embodiment of the apparatus shown in the previous figures pivoted to the sides.

DETAILED DESCRIPTION OF THE EMBODIMENTS OF THE INVENTION

Figure 1:
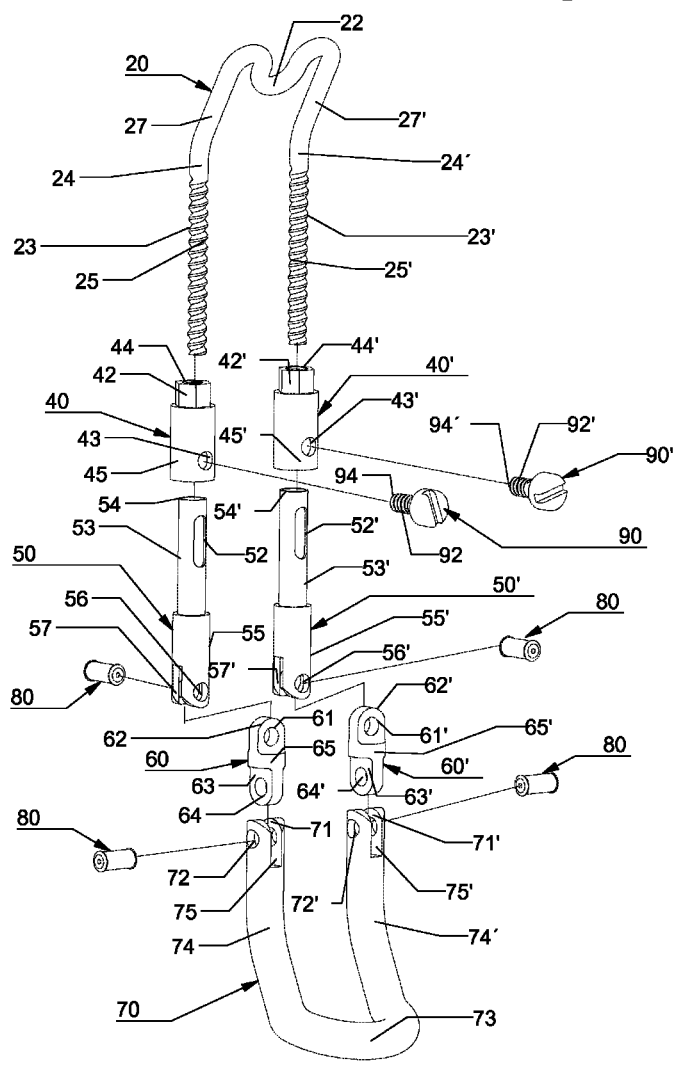
FIG. 1 represents an exploded isometric view showing the different components of an embodiment for the disk traction apparatus disclosed in the present application prior to being assembled.

Referring now to the drawings, where the present invention is generally referred to with numeral 10, it can be observed that it basically includes upper frame assembly 20 having substantially a U-shape, mounted to connector assemblies 40; 40' that in turn are mounted to frame assembly 20 with fastening members 90; 90'. Tubular assemblies 50; 50' are slidably mounted to assemblies 20 and 40. Tubular assemblies 50; 50' are pivotally (side movements) mounted to pivoting connector assemblies 60; 60' which are also pivotally (front-rear movements) connected to lower frame assembly 70.

Upper frame assembly 20 with elongated bars 23 and 23' each have straight non-threaded portions 24; 24', straight threaded portions 25; 25', and angled portions 27; 27', respectively, as best seen in FIG. 1. Assembly 20 has substantially U-shape configuration. Spacer member 22 is rigidly mounted to the upper ends of portions 27; 27' keeping bars 23; 23' at a parallel and spaced apart relationship with respect to each other. Spacer member 22 has a cooperating ergonomic shape compatible with the bone structure where it is going to be affixed.

For the purpose of this application, Applicant will refer to "lateral" or "sides" to positions or movements to the right or left of apparatus 10 from an upright elevational view as seen in FIG. 5. Whereas front and rear positions or movements will be those shown in FIG. 4.

Figure 3:
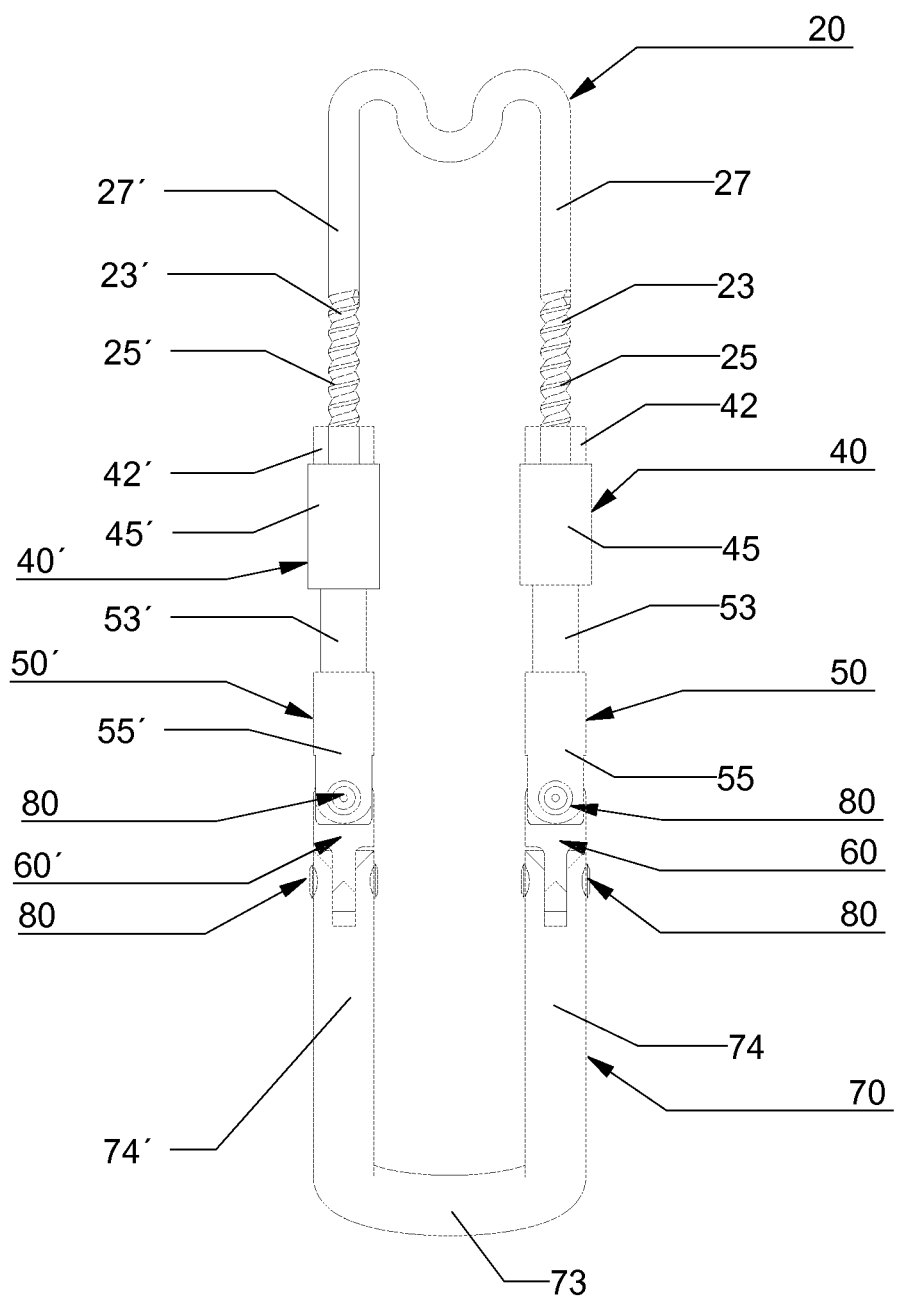
FIG. 3 is a rear elevational view of the device shown in FIG. 2.

Connector assemblies 40; 40' have an elongated shape with cylindrical portions 45; 45' at one end and polygonal portions 42; 42', at the other end, as best seen in FIGS. 1, 3F and 3G. Portion 45, has coaxial through opening 41 (only shown for portion 45, but portion 45' includes a similar coaxial through opening), as seen in FIG. 3G. Threaded through openings 43; 43' engage with fasteners 90; 90' that pass through one side of portions 45; 45' and through slots 52; 52' to exert a pressure against threaded bar 23; 23'; respectively. Portion 42 has coaxially disposed threaded through opening 44 (only shown for portion 42 but portion 42' includes a similar threaded through opening) for cooperative receiving threaded portions 25; 25'. Through opening 41 for connector assembly 40 (and similarly for 40') has an inner diameter that is larger that the inner diameter of threaded through opening 44 to allow a predetermined sliding movement of portion 53 (and 53'), as seen in FIG. 3B.

Polygonal portions 42; 42' can be readily actuated (rotated) using a cooperating wrench. Threaded through opening 44; 44' mate with threaded rod portions 25; 25' to advance the former along the latter securing a firm telescopic (adjustable to the needs of each patient) engagement between connector assemblies 40; 40' and upper frame assembly 20.

Tubular assemblies 50; 50' have an elongated shape with reduced portions 53; 53' and fork portions 55; 55', adjacent to each other, as best seen in FIGS. 1 and 3A. Longitudinal through bores 54; 54' partially receive threaded bars 23; 23', as best seen in FIG. 2A. Fork portions 55; 55' terminate with fork ends 57; 57'. Reduced portions 53; 53' include enlongated guiding slots 52; 52' to allow ends 94; 94' of shanks 92; 92' to pass herethrough and coact with threaded rod portions 25; 25' to secure or lock portions 45; 45' in place relative to portions 25; 25'. The dimensions of slots 52; 52' cooperate to guide shanks 92; 92' and limiting the slidable movement of tubular portions 53; 53'. Fork portions 55; 55' terminate with fork ends 57; 57' include through holes 56; 56'.

Pivoting connector assemblies 60; 60' include ears 62; 62' each having through holes 61; 61' and ears 63; 63' each having through holes 64; 64', as seen in FIG. 1. Cylindrical bodies 65; 65' provide the structure for the transition from ears 62; 62' to ears 63; 63'. Ears 62; 62' are disposed at 90 degrees with respect to ears 63; 63'. Ears 62; 62' are received within fork ends 57; 57' of fork portions 55; 55', respectively. Through holes 61; 61' cooperatively coincide with through holes 56; 56' with cooperative dimensions to receive rivet pins 80; 80; therethrough. Rivet pins 80; 80' are cylindrical and sized to extend beyond through holes 56; 56'. Once inside holes 56; 56' are flattened to prevent their dislodgement. Fork portions 55; 55' and tubular assemblies 50; 50' move to a maximum angle of approximately five degrees. The lateral movement of assemblies 50; 50' with respect to connector assemblies 60; 60' is limited, in addition to the dimensional limitation of slots 52; 52' and the inner walls of longitudinal through opening 41; 41'. Ears 63; 63' have similar through holes 64; 64' that cooperate with through holes 72; 72; of lower frame assembly 70'.

Lower frame assembly 70 has elongated members 74; 74' having fork connector terminations 75; 75' having fork connector ends 71; 71' with transversally disposed through holes 72; 72'. Assembly 70 has a substantially U-shape configuration. Members 74; 74' are connected through spacer member 73 that keeps the former in a rigid parallel and spaced apart relationship. Ends 71; 71' receive ears 63; 63' and rivet pins 80; 80' are passed through through holes 64; 64' to allow tubular assemblies 50; 50' to pivot forward and rearwardly with respect to the plane of apparatus 10 as shown in FIG. 4.

When rivet pins 80 have cooperative dimensions so that when they are passed through through holes 56; 56'; 61; 61'; 63; 63'; 72 and 72' they protrude slightly to permit a surgeon to hit them deforming the ends (riveting). This permits the joined members to pivot or rotate freely without being dislodged.

A physician will affix apparatus 10 to a patient's spinal bones using conventional means such as surgical wires and/or screws. With the present invention a patient can be provided with support and distention for his/her vertebrae of approximately five degrees per vertebra.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. An apparatus for treating spinal vertebrae, comprising:
A) a first U-shape frame assembly having first and second elongated bar members extending at a parallel and spaced apart relationship with respect to each other defining a first plane and said first and second elongated bar members having first and second threaded portions, respectively;
B) first and second elongated connector assemblies being at a parallel and spaced apart relationship with respect to each other and having third and fourth ends, said third ends including internal threaded openings mounted to said first and second threaded portions, respectively;
C) first and second parallel and spaced apart elongated tubular assemblies, having first and second longitudinal slots, and being telescopically and slidably mounted to said first and second bar members and partially housed by said first and second connector assemblies, respectively and further including first and second fastening members for mounting said first and second connector assemblies to said first and second threaded portions and passing through said slots;
D) first and second parallel and spaced apart and parallel elongated pivoting connector assemblies pivotally mounted to said first and second tubular assemblies, respectively, to permit a predetermined coplanar lateral movement of said first and second tubular assemblies with respect to said pivotally connector assemblies;
E) a second U-shape frame assembly having third and fourth elongated bar members extending at a parallel and spaced apart relationship with respect to each other defining a second plane and being pivotally mounted to said first and second elongated pivoting connector assemblies, respectively, to permit a predetermined movement of said second U-shaped frame member from a coplanar position with respect to the first plane tubular to different predetermined planes; and
F) means for mounting said apparatus to the spinal bones of a patient so that predetermined mechanical support and distention can be selectively and gradually applied to predetermined vertebrae as deemed necessary by the operating surgeon.

2. An apparatus for treating spinal vertebrae, comprising:
A) a first frame assembly having first and second elongated members each including first and second ends, and a first spacer member rigidly mounted to said first ends so that said first and second elongated members are kept at a parallel and spaced apart relationship with respect to each other, and said second ends each includes an external threaded portion;
B) first and second elongated connector assemblies each having a polygonal portion and a cylindrical portion, said polygonal portion including a coaxially disposed threaded through opening with a first internal diameter for cooperatively receiving said second ends, and each of said cylindrical portions including a coaxially disposed through opening, having a second internal diameter that is larger than said first internal diameter, connected to said threaded through opening, said polygonal portion being designed and adapted to receive a cooperating wrench for imparting a rotational force;

C) first and second elongated tubular assemblies each having first and second slots, third and fourth ends, said third ends being telescopically and slidably mounted within said coaxially disposed through openings including first and second fastening members passing through said slots to keep said first and second connector assembly at a predetermined relative movement with respect to said first and second threaded portions and said fourth ends having each a first fork termination with a transversal first through hole therethrough;

D) first and second elongated pivoting connector assemblies each having fifth and sixth ends, said fifth ends each defining first ears with second through holes transversally disposed and said sixth ends defining second ears with third through holes transversally disposed and said second ears being disposed at 90 degrees with respect to said first ears;

E) first and second pins passed through said second through holes to keep said fifth ends and said first fork termination pivotally mounted to each other, so that said first frame assembly, elongated connector and tubular assemblies pivotally move laterally and coplanarly with respect to said pivoting connector assemblies in a first plane;

F) a second frame assembly having third and fourth elongated members each including seventh and eighth ends, and a second spacer member mounted to said seventh ends for keeping said third and fourth elongated members at a parallel spaced apart relationship with respect to each other, said eighth ends including a second fork termination with transversally disposed fourth throughholes;

G) third and fourth pins passed through said fourth through holes to keep said sixth ends and said second fork termination pivotally mounted to each other so that said second frame moves from a coplanar position with respect to said first plane to predetermined forward and rearward plane positions; and H) means for mounting said apparatus to the spinal bones of a patient so that predetermined mechanical support and distention can be selectively and gradually applied to predetermined vertebrae as deemed necessary by the operating surgeon.

\* \* \* \* \*